United States Patent [19]

Rapkin et al.

[11] 4,405,718

[45] Sep. 20, 1983

[54] METHOD AND COMPOSITION FOR UROBILINOGEN CONTROL STANDARD

[75] Inventors: Myron C. Rapkin, Elkhart, Ind.; David L. Tabb, Beaumont, Tex.

[73] Assignee: Miles Laboratories, Inc., Elkhart, Ind.

[21] Appl. No.: 284,556

[22] Filed: Jul. 20, 1981

[51] Int. Cl.³ ................... G01N 33/48; G01N 33/72
[52] U.S. Cl. ........................................ 436/8; 436/12; 436/96; 436/97
[58] Field of Search ............ 252/408; 23/230 B; 436/8, 12, 96, 97

[56] References Cited

U.S. PATENT DOCUMENTS

| | | | |
|---|---|---|---|
| 2,057,948 | 10/1936 | Herdieckerhoff et al. | 260/319.1 |
| 2,811,530 | 10/1957 | Poizat et al. | 260/319.1 |
| 3,012,040 | 12/1961 | Lind et al. | 260/326.19 |
| 3,446,599 | 5/1969 | Shand et al. | 252/408 |
| 3,630,680 | 12/1971 | Rittersdorf et al. | 252/408 |
| 3,814,586 | 6/1974 | Frazer et al. | 23/230 B |
| 3,853,466 | 12/1974 | Rittersdorf et al. | 23/230 B |
| 3,989,462 | 11/1976 | Hirsch | 23/230 B |
| 4,038,031 | 7/1977 | Lam | 252/408 |
| 4,158,546 | 6/1979 | Lam et al. | 252/408 |

FOREIGN PATENT DOCUMENTS 2926833 4/1980 Fed. Rep. of Germany.

OTHER PUBLICATIONS

Chemical Abstracts, vol. 93, p. 344, Abstract 22148b, Daunora et al. (1980).

Chemical Abstracts, vol. 18 (9), pp. 1294–1296, Blaike et al.

*Primary Examiner*—Benjamin R. Padgett
*Assistant Examiner*—M. Moskowitz
*Attorney, Agent, or Firm*—James D. McNeil

[57] ABSTRACT

A urobilinogen control standard composition, control standard device and a method for preparing such composition are disclosed. The composition comprises a substituted indole:nonionic detergent solution which is reactive with p-diethylaminobenzaldehyde and hydrochloric acid. The composition is produced by dissolving the substituted indole in a selected nonionic detergent and diluting the solution to a predetermined level. The device is a carrier matrix impregnated with a solution of a substituted indole and a nonionic detergent.

11 Claims, No Drawings

METHOD AND COMPOSITION FOR UROBILINOGEN CONTROL STANDARD

BACKGROUND OF THE INVENTION

It is known that various disease conditions cause abnormal levels of urobilinogen in urine, e.g., hemolytic and hepatic diseases, bilary obstruction and other lower and bile duct dysfunctions. It is recognized that the presence of urobilinogen at elevated level indicates an abnormal physiological state which requires further diagnostic procedures.

The standard test for detecting urobilinogen concentration in urine is the so-called "Ehrlich reaction", which utilizes an aqueous solution of p-dimethylaminobenzaldehyde and hydrochloric acid, referred to as Ehrlich's reagent. Urobilinogen is normally found in urine in small amounts e.g., 0.1 to 2 Ehrlich Units. One Ehrlich Unit is defined as one milligram (mg) of urobilinogen per deciliter of sample. [See *Clinical Diagnosis by Laboratory Methods*, p. 703, Davidsohn and Henry (1969)]. In the presence of urobilinogen, a complex of Ehrlich's reagent is produced, having absorption in the visible spectrum. The color produced can be various shades of reddish-brown, depending on the presence of interfering substances present in the urine, e.g., p-aminosalicylic acid, porphobilinogen and urea.

Currently there are available sophisticated biochemical systems which can be incorporated into dry, dip-and-read reagent strip devices, used in solution or suspension techniques, or in conjunction with spectrophotometrics and other read-out systems. Strips comprise a bibulous and nonbibulous strip, having at one end a carrier portion impregnated with an appropriate testing composition.

These dip-and-read reagent strips can incorporate Ehrlich's reagent, i.e., p-dimethylaminobenzaldehyde and hydrochloric acid. The strip is dipped into urine, and the color developed is then compared with a standard color chart prepared for use in conjunction with the reagent strip. A negative or positive for urobilinogen is obtained; if positive the approximate amount of urobilinogen present, expressed in Ehrlich Units, can be determined by comparing to a printed color chart as described hereinafter.

In carrying out testing of urine samples for urobilinogen, whether by dip-and-read strips or other techniques, it is necessary to use control solutions which are capable of producing the same color reaction produced by the presence of urobilinogen. Such controls are useful in checking the instrument used, or if the test involves human visual observation, in checking the skill of the technician, i.e., as an "unknown". In addition, controls are useful for educational purposes, e.g., in instructing technicians in carrying out urobilinogen tests.

In order to be most useful, especially in conducting "blind" skill tests, urobilinogen controls must not only closely match the color produced by the presence of urobilinogen in urine, but also must not have olfactory properties noticeably different from urine olfactory properties, and must be light-stable for at least 4 hours and preferably for 48 hours.

It is common that such controls involve the use of the substance which is being tested; however, because urobilinogen is unstable and generally unavailable, other chemical compounds have been used as a control material. Compounds which have been used as a urobilinogen control are indoles. Although it has been known that indoles, freshly prepared, do react with Ehrlich's reagent to produce reddish-brown colors that closely resemble the colors formed by urobilinogen present in urine and Ehrlich's reagent, indoles suffer the disadvantage of possessing a characteristic, highly noticable unpleasant odor; are relatively insoluble in aqueous solutions; are lightsensitive and are very unstable.

The present invention provides a method and improved indole composition for use as a urobilinogen control standard which overcomes these problems.

SUMMARY OF THE INVENTION

The present invention is directed to a method, and a composition and a device involving a urobilinogen control standard for use in testing for the presence of urobilinogen in a urine sample. The composition is a substituted indole:non-ionic detergent solid solution. The method involves dissolving a substituted indole in a nonionic detergent which is an alkanolamide, an ethoxy alkanolamide, an ethoxy phenol or an ethoxy fatty alcohol. The device comprises a carrier matrix impregnated with a mixture of a substituted indole and a nonionic detergent.

DETAILED DESCRIPTION OF THE INVENTION

The urobilinogen control standards of the present invention are prepared by dissolving a substituted indole in a nonionic detergent. The indole-nonionic detergent solution can be used as a urobilinogen control by adding the mixture to distilled water and using the solution as a control standard or used to impregnate a carrier matrix. The indole solution can be solidified and dry blended with solid diluents and formed into tablets or capsules by conventional processing techniques.

The indole can be any substituted indole which will react with a modified Ehrlich's reagent (p-diethylaminobenzaldehyde and hydrochloric acid) to produce a reddish-brown color which can be correlated to the color produced with the same reagent and urobilinogen present in a test sample.

Suitable substituted indoles which react with a modified Ehrlich's reagent according to the present invention have the formula:

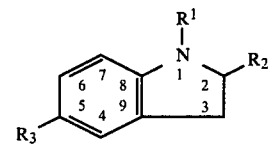

wherein $R_1$ and $R_2$ are the same or different and are H or a substituted or unsubstituted $C_1$-$C_4$ alkyl, and $R_3$ is H, a substituted or unsubstituted $C_1$-$C_4$ alkyl, alkoxy, or halogen with the proviso that $R_1$, $R_2$ and $R_3$ cannot simultaneously be hydrogen.

Suitable substituted indoles include: 2-methylindole, 1,2-dimethylindole, 2,5-dimethylindole, 2-methyl-5-methoxyindole and 5-methoxyindole.

The indoles are dissolved in a nonionic detergent to produce an indole solution which can be up to 10 percent w/w indole. Although the indoles which are suitable for use in the present invention are relatively insoluble in water, the indole-detergent solutions formed are easily solubilized in water. The indole-detergent solution can then be further diluted, e.g., to 1 percent, 0.1 percent and 0.01 percent, for use as a control standard. The control standards thus prepared simulate a urobilinogen concentration range of from about 2 to about 12 Ehrlich Units.

It has been determined that suitable nonionic detergents for use in the present invention are: alkanolamides; ethoxy alkanolamides; ethoxy phenols and ethoxy fatty alcohols.

Liquid preparations are preferably incorporated with a carrier matrix in strip format. The term carrier matrix can be envisioned to refer to bibulous and nonbibulous matrices which are insoluble in and maintain their structural integrity when exposed to water or physiological fluids. Suitable bibulous matrices which can be used include paper, cellulose, wood, synthetic resin fleeces, woven and nonwoven fabrics and the like. Nonbibulous matrices include organoplastic materials, such as polystyrene, polypropylene or the like. When a bibulous matrix is employed, the matrix is advantageously affixed, such as by double-faced adhesive tape, to an insoluble support member, such as an organoplastic strip, for ease of use.

Alternatively, the compositions of the invention can be embodied in a carrier taking the form of a pressed or molded tablet containing conventional carrier material. Such devices can be prepared by contacting a carrier, such as a matrix with the indole detergent solution. When this contacting is by impregnation with a solution of the composition according to the invention, the carrier so contacted is then dried. In addition to impregnation, the devices of the present invention can be made by other suitable techniques such as printing or spraying the composition onto a substrate or matrix. The solvent used in preparing solutions for the method can be distilled or deionized water.

The following Examples illustrate the preparation and use of urobilinogen control standards according to the present invention.

EXAMPLE 1

A 10.0 g portion of a polyethoxy fatty alcohol, commercially available from GAF, New York, N.Y., under the trade designation Emulphor ON870, was heated to 40° C. A 1.0 g portion of 2,5 dimethylindole was mixed with and dissolved in the heated detergent. After the 2,5-dimethylindole was dissolved, the mixture was allowed to cool and solidify. The characteristic indole odor was substantially eliminated.

A series of 2,5-dimethylindole detergent solutions was prepared by similar procedures.

In order to determine the suitability of the indole:detergent solutions for use as a urobilinogen control standard, the solutions were tested as described below.

A series of dip-and-read strips was prepared by impregnating the strips with a modified Ehrlich's reagent (p-diethylaminobenzaldehyde) in a strongly acidic environment (HCl).

Urobilinogen color charts were prepared as described below, using a urine sample containing an abnormally elevated urobilinogen level, from a patient with a liver disorder which produces large amounts of urobilinogen. The urobilinogen level of the urine was assayed by known wet chemistry methods described in *Clinical Diagnosis by Laboratory Methods*, pp. 703–705, Davidsohn and Henry (1969).

Aliquots of the urine were then diluted with "normal" urine (containing not greater than 2 Ehrlich Units) to selected levels of 0.1, 1.0, 2.0, 4.0, 8.0 and 12.0 Ehrlich Units. The diluted samples constitute an array of samples suitable for measuring urobilinogen level in urine. These samples containing unstable urobilinogen were stored over dry ice.

A printed color standard was prepared for each of the above levels as follows. The diluted samples (stored over dry ice) were transported to a printer skilled in color matching. A representative standard, e.g., 2 Ehrlich Units, was thawed and allowed to equilibrate at room temperature. A strip was dipped into the 2 Ehrlich Unit urine sample, and the reddish-brown color which developed on the strip was observed by a chemist and the printer. An ink formulation was compounded to closely match the color which developed on the strip. This empirical color-matching procedure was repeated for each Ehrlich Unit level referred to above.

The indole:detergent solutions of the present invention were tested as urobilinogen control standards against the above urobilinogen-produced color standards as follows. The 1 percent 2,5-dimethylindole:detergent mixture, prepared as described earlier, was diluted with distilled water to 0.1 and 0.01 percent solutions.

The colors which developed on the strips dipped into the aqueous solution of 1 percent, 0.1 percent and 0.01 percent indole:detergent solutions were examined to determine whether the colors matched the various reddish-brown shades produced by the urobilinogen containing urine speciments.

The tests results obtained are summarized in Table 1 below.

TABLE 1

| Detergent | Color Developed (1%) | Color Developed (0.1%) | Color Developed (.01%) |
|---|---|---|---|
| Ethoxylated fatty alcohol | pink (atypical) | reddish-brown (typical) | reddish-brown (typical) |
| Ethoxylated phenol | pink (atypical) | reddish-brown (typical) | reddish-brown (typical) |
| Ethoxylated alcohol | reddish-brown (typical) | reddish-brown (typical) | |
| Ethoxylated alkanolamide | pink (atypical) | reddish-brown (typical) | |
| Ethoxylated phenol | pink (atypical) | reddish-brown (typical) | |
| Alkanolamide | pink (atypical) | reddish-brown (typical) | |
| Alkanolamide | reddish-brown (typical) | reddish-brown (typical) | |

As shown by the data summarized in Table 1, each of the indole:detergent solutions tested was usable as a urobilinogen control standard at a dilution in the range of 1 percent, 0.1 percent and 0.01 percent indole. The dilution which produces a usable urobilinogen control standard is easily determined by one skilled in the art, by mixing up various dilutions, as described above, and testing the solutions against known urobilinogen-containing samples.

We claim:

1. A method of preparing a substantially odor-free urobilinogen-free urobilinogen control standard for use in testing for the presence of urobilinogen in a urine sample which closely simulates the properties of a urobilinogen-containing urine sample when reacted with a urobilinogen assay system, which comprises dissolving a substituted indole having the formula:

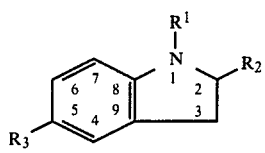

wherein $R_1$ and $R_2$ are the same or different and are H or unsubstituted $C_1$-$C_4$ alkyl, and $R_3$ is H, unsubstituted $C_1$-$C_4$ alkyl, unsubstituted $C_1$-$C_4$ alkoxy, or halogen with the proviso that $R_1$, $R_2$ and $R_3$ cannot simultaneously be hydrogen, in a nonionic detergent selected from the group consisting of an alkanolamide, an ethoxy alkanolamide, and ethoxy phenol and an ethoxy fatty alcohol.

2. A method as claimed in claim 1 wherein the substituted indole is selected from the group consisting of 2-methylindole, 1,2-dimethylindole, 2,5-dimethylindole, 2-methyl-5-methoxy indole and 5-methoxyindole.

3. A method as claimed in claim 2 wherein the indole is 2,5-dimethylindole.

4. A method as claimed in claim 1 wherein the urobilinogen assay system is p-diethylaminobenzaldehyde-hydrochloric acid.

5. A method as claimed in claim 1 wherein after the substituted indole is dissolved in said detergent, the solution is solidified to form a solid urobilinogen control standard.

6. A method as claimed in claim 1 wherein after the substituted indole is dissolved in said detergent, the solution is solidified and added to water to form a liquid urobilinogen control standard.

7. A urobilinogen-free urobilinogen control standard which comprises a compound of the formula:

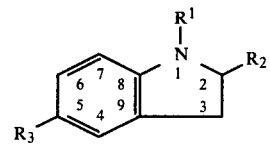

wherein $R_1$ and $R_2$ are the same or different and are H or unsubstituted $C_1$-$C_4$ alkyl, and $R_3$ is H, unsubstituted $C_1$-$C_4$ alkyl, unsubstituted $C_1$-$C_4$ alkoxy, or halogen with the proviso that $R_1$, $R_2$ and $R_3$ cannot simultaneously be hydrogen, with a nonionic detergent selected from the group consisting of an alkanolamide, an ethoxy alkanolamide, an ethoxy phenol and an ethoxy fatty alcohol.

8. A urobilinogen control standard as claimed in claim 7 wherein the nonionic detergent is selected from the group consisting of an alkanolamide, an ethoxy alkanolamide, an ethoxy phenol and an ethoxy fatty alcohol.

9. A urobilinogen control standard as claimed in claim 8 wherein the indole is 2,5-dimethylindole.

10. A urobilinogen control standard as claimed in claim 8 wherein the indole:detergent solid solution is dissolved in water.

11. A urobilinogen-free urobilinogen control standard device which comprises a carrier and, incorporated therewith, a predetermined amount of the composition of claim 7.

* * * * *